US007668735B2

(12) United States Patent
Grace et al.

(10) Patent No.: US 7,668,735 B2
(45) Date of Patent: Feb. 23, 2010

(54) COMPENSATED ELECTRONIC CONSULTS

(75) Inventors: Joseph P. Grace, Matinecock, NY (US); William R. Grace, Jr., New York, NY (US)

(73) Assignee: MDRxDirect Inc., New York, NY (US)

( * ) Notice: Subject to any disclaimer, the term of this patent is extended or adjusted under 35 U.S.C. 154(b) by 318 days.

(21) Appl. No.: 11/441,434

(22) Filed: May 25, 2006

(65) Prior Publication Data

US 2006/0218009 A1  Sep. 28, 2006

Related U.S. Application Data

(63) Continuation-in-part of application No. 11/333,881, filed on Jan. 18, 2006, now abandoned, and a continuation-in-part of application No. 10/448,939, filed on May 30, 2003, now abandoned.

(51) Int. Cl.
G06Q 50/00 (2006.01)

(52) U.S. Cl. .......................................... 705/2; 705/14.1

(58) Field of Classification Search ............... 705/14, 705/2, 3; 463/20, 40; 707/3; 706/45; 725/23; 434/322, 350
See application file for complete search history.

(56) References Cited

U.S. PATENT DOCUMENTS

| | | | | |
|---|---|---|---|---|
| 5,517,405 | A * | 5/1996 | McAndrew et al. | 706/45 |
| 5,799,981 | A | 9/1998 | Tung et al. | |
| 5,819,228 | A * | 10/1998 | Spiro | 705/2 |
| 6,014,634 | A | 1/2000 | Scroggie et al. | |
| 6,035,276 | A * | 3/2000 | Newman et al. | 705/2 |
| 6,067,525 | A | 5/2000 | Johnson et al. | |
| 6,076,088 | A | 6/2000 | Paik et al. | |
| 6,256,614 | B1 * | 7/2001 | Wecker et al. | 705/14 |
| 6,272,481 | B1 | 8/2001 | Lawrence et al. | |
| 2001/0032125 | A1 * | 10/2001 | Bhan et al. | 705/14 |
| 2001/0041991 | A1 * | 11/2001 | Segal et al. | 705/3 |
| 2002/0065683 | A1 | 5/2002 | Pham et al. | |
| 2002/0116256 | A1 * | 8/2002 | De Rafael et al. | 705/14 |
| 2002/0133375 | A1 * | 9/2002 | Moore et al. | 705/2 |
| 2002/0173990 | A1 | 11/2002 | Marasco | |
| 2002/0188498 | A1 | 12/2002 | Stoloff et al. | |

(Continued)

FOREIGN PATENT DOCUMENTS

WO    WO 0167333 A1 * 9/2001

(Continued)

OTHER PUBLICATIONS

Khan, Z. M., et al., "Fax Technology for Collecting Outcomes Data in a Computer Database," American Journal of Health System Pharmacy, Dec. 15, 1999, 56 (24) pp. 2540-2542, ISSN 1079-2082, Journal Code 9503023, Dialog File 155, Acc. No. 10-5119135.

(Continued)

Primary Examiner—Gerald J. O'Connor
Assistant Examiner—Natalie A Pass
(74) Attorney, Agent, or Firm—Bryan Cave LLP

(57) ABSTRACT

The present invention relates to a system and method for providing health care information to health care providers and for obtaining information pertaining to the practice of a health care provider by providing incentives for provision of such information.

17 Claims, 9 Drawing Sheets

U.S. PATENT DOCUMENTS

| | | | |
|---|---|---|---|
| 2003/0027635 A1 | 2/2003 | Walker et al. | |
| 2003/0061096 A1 | 3/2003 | Gallivan et al. | |
| 2003/0064788 A1* | 4/2003 | Walker et al. | 463/20 |
| 2003/0074234 A1 | 4/2003 | Stasny | |
| 2003/0088479 A1* | 5/2003 | Wooten et al. | 705/26 |
| 2003/0126122 A1* | 7/2003 | Bosley et al. | 707/3 |
| 2003/0163352 A1* | 8/2003 | Surpin et al. | 705/14 |
| 2004/0225529 A1 | 11/2004 | Snyder et al. | |
| 2004/0243437 A1 | 12/2004 | Grace et al. | |
| 2005/0228718 A1* | 10/2005 | Austin | 705/14 |
| 2005/0273426 A1 | 12/2005 | Hammock | |

FOREIGN PATENT DOCUMENTS

| | | |
|---|---|---|
| WO | WO 02/11030 | 2/2002 |

OTHER PUBLICATIONS

Corcoran et al., "Enhancing ROI though Exhibiting" MM&M Aug. 1996, pp. 41, 42 and 44.

OIG Advisory Opinion No. 04-03 Jun. 1, 2004 Office of Inspector General, U.S. Department of Health & Human Services, (printed from http://oig.hhs.gov/fraud/docs/advisoryopinions/2004/ao0403.pdf on Jan. 13, 2008).

* cited by examiner

Where a physician's time and clinical Insights are valued.
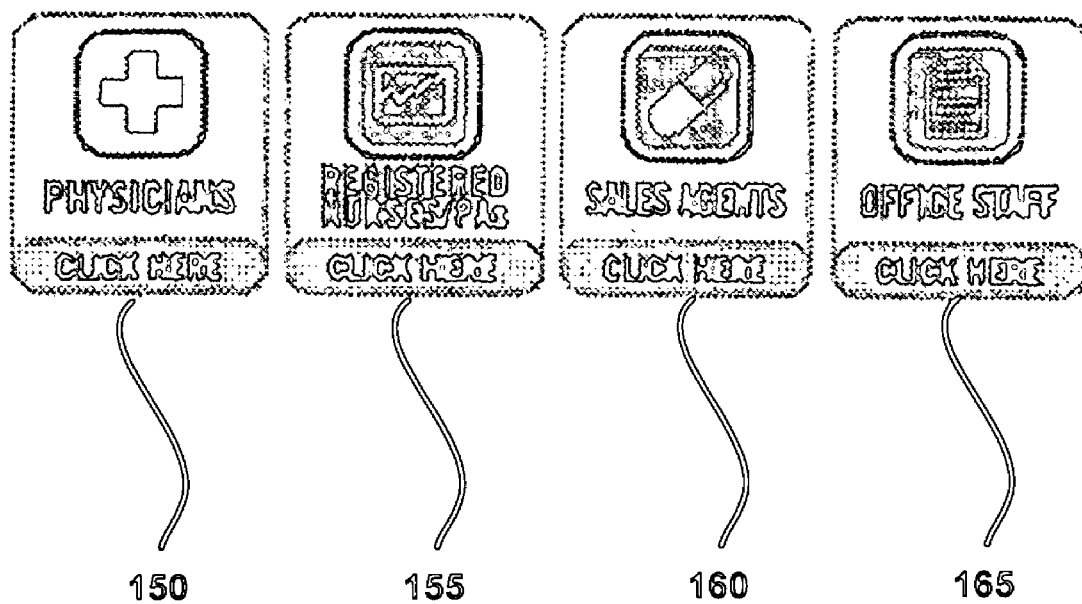
Fig. 3

E-Consults

Welcome to the MDRxDirect E-Consult Center

MDRxDirect E-Consults provide a quick, efficient means for physicians to provide feedback to pharmaceutical and other medical companies. These E-Consults take only a few minutes to complete, and you will receive compensation for your valuable time.

185

E-Consults Published by Glaxo Wellcome:

| Title (click to take E-Consult) | Description | Date Published |
|---|---|---|
| Newly approved Leukoease for control of Asthma | Anti-leukotriene or leukotriene modifiers fight potent chemicals within the body called leukotriene... | 1/15/2003 |
| Oxaliplatin and Colorectal Cancer | Please take the time to think about the information just presented to you in the E-Consult and cond... | 1/15/2003 |

*Fig. 5*

COMPENSATED ELECTRONIC CONSULTS

CROSS REFERENCE TO RELATED APPLICATION

This continuation-in-part application claims benefit of U.S. patent application Ser. No. 11/333,881, filed Jan. 18, 2006 and U.S. patent application Ser. No. 10/448,939, filed May 30, 2003. The disclosure of each such application is hereby incorporated by reference in its entirety where appropriate for teachings of additional or alternative details, features, and/or technical background, and priority is asserted from each.

BACKGROUND OF THE INVENTION

1. Field of the Invention

The present invention relates generally to distance electronic consults and, more particularly, to a system and method for providing health care information customized to the profile of a health care provider, wherein the health care provider is compensated for providing clinical insights on health care information retrieved by the health care provider over the system and/or information on the health care provider's health care practice.

2. Description of the Related Art

Medical doctors, physician assistants, registered nurses, licensed practical nurses, pharmacists, optometrists, naturopaths, osteopaths, chiropractors, and other health care providers are ever increasingly faced with a growing body of technical literature related to the health care needs of their patients. Pressures to reduce costs in the provision of health care services, however, has resulted in many health care providers having to expend significantly longer periods of time in pursuit of their occupations than in the past to obtain the same desired income. The latter has resulted in many health care professionals facing a dearth of time in which to obtain the knowledge necessary for them to stay current in their health care specialties.

A primary source of medical information is the technical literature which reports the results of studies and investigations undertaken by different researchers. Unfortunately, most health care providers today simply do not have the time to objectively compare a report on a medical topic made by one investigative group with those made by other investigative groups in order to discern a consensus on the topic. They often therefore depend on review articles that attempt to summarize the body of information pertaining to any particular medical topic. Unfortunately published review articles, like the published individual investigative report, do not provide the health care provider with an optimal way of questioning the results of a study, or the conclusions of an author. In truth for the most part, the health care provider generally does not have the capability of making inquiries in light of the health care provider's own experiences except through letters to the editor and the like. Medical knowledge is also hampered in that the authors of an article are unlikely to gain substantial input from the reading audience.

Many health care providers today gain a substantial amount of their continuing medical education through review seminars. Live review seminars provide the health care provider with the opportunity to field questions to, and exchange information with, the provider of the seminar. Many live review seminars are provided by manufacturers of health care products and services. Such companies also provide for live interaction with their representatives, such as detail representatives of a pharmaceutical company. The problem with these sources of information is that seminars and detailing may not be offered at an optimum time given the individual health care provider's schedule. For example, a physician can not take the time to attend a live seminar course or meet with a detail person when one of the physician's patients is in immediate need of medical care. Further, a physician is often unable to participate in face-to-face medical information exchanges due to patient scheduling conflicts.

There is a significant desire by manufacturers of health care products and providers of health care services that certain information pertaining to their products be disseminated. Such manufacturers also know that the best method of disseminating medical information to health care providers is a one-on-one exchange wherein the health care provider is provided the opportunity to exchange his or her real-life experiences with a particular treatment protocol, or an alternative treatment protocols. Such an interchange not only allows the manufacturer to address concerns by the health care provider in regard to the manufacturer's information, but also allows the manufacturer to learn the most pressing educational needs of the health care provider. For example, it makes little sense to provide information pertaining to the benefits of a drug designed to treat benign prostrate hypertrophy when a physician's practice consists entirely of female patents.

While a one-to-one exchange is extremely useful both for the manufacturer/service provider and the health care provider, as discussed above such exchanges are becoming far more difficult due to the ever increasing time demands on health care providers. For example, it has been reported that nearly half of all visits made to a physicians' offices by drug detail representatives do not result in the representative actually speaking to the physician. Of those pharmaceutical detailers who get an audience with a physician, it has been estimated that on average the detail lasts for less than two minutes, an insignificant time for a true information exchange to take place. Given the economics of spending time on non-reimbursed educational exchanges versus providing fee-for-service exchanges with patients in a health care system micro-managed to limit reimbursement for medical services, many health care providers simply are not provided the incentive to spend time on educational exchanges.

Accordingly, there is a significant need on behalf of both manufacturers of health care products and purveyors of health care services on the one hand, and health care providers on the other hand, to be able to efficiently communicate with one another at opportune times for the health care provider. There is also a need to provide incentives to health care providers to take the time to adequately apprise themselves of new information pertaining to medical therapies, and medical products/services.

SUMMARY OF THE INVENTION

A system and method is disclosed for providing customized medical information to health care providers which allows for an interchange between the health care provider and the information provider and which provides incentives for the health care provider to participate in the information exchange.

In one embodiment of the invention there is provided a system and method for providing medical information selections which are tailored to a health care provider's educational and practice profile. A profile of the health care provider can be developed by obtaining information pertaining to characteristics of the health care provider from the health care provider directly, and/or indirectly from the type of information sought and the feedback obtained by the information purveyor from the health care provider.

In another embodiment, there is provided a system and method that provides incentives for the health care provider to provide feedback to the information purveyor prior to, during, and/or after reviewing the information which is retrieved by the health care provider. In one preferred embodiment, the incentive is awarded when the health care provider provides information pertaining to the health care provider's practice with respect to the information provided (or to be provided), or less preferably, with respect to health issues which are diverse from the information provided. In such preferred embodiment, the information purveyor obtains information useful to it in determining future marketing plans and possibly research endeavors.

In yet another embodiment of the invention the information is provided to the health care provider only upon registration of the health care provider with the information purveyor, or a third party that distributes information of the information purveyor. Registration may comprise a verification process that verifies that the health care provider has the desired qualifications for obtaining the information. For example, the system may request that a person indicating that they are a medical doctor provide their State License number, their Drug Enforcement Number, their birth date, the medical school from which they graduated, the location of their residency program, etc. Such information provided can be checked against public databases to determine whether such information is valid. A lesser check, as for example using known algorithms that indicate whether a DEA number is valid, may also be employed for verification purposes.

As would be understood by one of ordinary skill in the art, verification of the qualifications of the health care provider may be important to the type of information proffered to the health care provider for review. For example, an anesthesiologist would be expected to have significantly different educational needs with respect to information on medical supplies, than a podiatrist.

Use after registration may entail verification that that the person indicating that they are the registered health care provider is indeed the registered health care provider. For example, the DEA number of physician, a system-provided registration code, and knowledge likely known only by the physician, such as the physician's situs of residency training, might be used to verify that the person entering the system is indeed the person indicated.

In one preferred embodiment, information supplied by the health care provider and/or captured during interaction with the system is stored and used to develop a profile which is used to filter information that is ultimately proffered to the health care provider's viewing/sensing. Health care provider information may include, for example, information pertaining to the interests of the health care provider, information pertaining to the personal history of the health care provider (e.g., birth date, schools attended, diplomas received, contact information, family history, etc.), websites explored by the health care provider, responses to information provider queries, and a history of use of the system. Such health care provider information may be advantageously used in developing a profile of the health care provider to proffer a menu of informational materials that are most likely to be viewed by the health care provider. For example, a dentist would be much more likely to review information pertaining to drugs used in dentistry rather than drugs used in the treatment of psoriasis.

Topic information provided to the health care provider can be of any type of information, but preferably related to the health care provider's professional field. Topic information may comprise, for example, information pertaining to drugs that are used by professionals in the health care provider's professional field, information pertaining to medical devices or supplies that are commonly used by health care providers in the health care provider's professional field, information pertaining to medical therapies often encountered by health care professionals in such professional field, summaries and reviews of current thought related to a treatment protocol or disease state generally of interest to the persons in the health care professional's professional field, comparative information with respect to alternative treatment protocols used in the art, promotions, insurance information, health care news and FDA announcements of news of interest to persons in the health care professional's professional field. Preferably topic information is provided in a manner such that the health care professional can interact with the system to respond to queries, and/or to pose questions for resolution either in real time or at a later time.

Preferably information is provided free of charge to the health care provider (although a charge can be incurred to retrieve the data, or if response to one or more queries of the information purveyor is not made by the health care provider). In a preferred method and system, information is provided free of charge regardless of the interactions of the health care provider with the system, however the health care provider is provided an incentive to respond to professional queries of the information purveyor, in particular with respect to the health care provider's practice, patients/clients/customers, and the health care provider's professional judgment with respect to matters of interest to the information purveyor or to a third party that distributes the information of the information purveyor. Thus an interface for the health care provider to answer on-line survey questions is provided.

In one embodiment the response to queries/questions posed by the information purveyor during the information presentation is used to dynamically generate survey queries which will aid the information purveyor in its primary business. For example, if during the presentation the health care provider indicates that the health care provider regularly treats asthma patients and has used certain anti-asthma drugs in the treatment of asthma, at the end of the presentation queries related to what anti-asthma drug the health care provider typically uses, the percent of patients diagnosed with asthma of a particular age group which the health care provider treats, the health care provider's multi-controller approach to treating asthmatic patients, the health care providers observations with respect to certain patient populations, etc. may be proposed. As would be understood by one of ordinary skill in the art, such individual practice information when aggregated can provide the information purveyor, and others seeking such information from the information purveyor, with extremely valuable information which may be quite useful in developing new research studies, improving the marketing of health care products, uncovering previously unrecognized drug interactions/side effects, uncovering defects in therapeutic devices, and discovering metabolic polymorphisms in select patient populations, etc.

Response to the professional survey queries/questions preferably results in an incentive being provided to the health care provider. For example, the health care provider may be provided a stipend for the health care provider's medical input with respect to the health care provider's experiences in the health care provider's practice. In this sense, the health care provider is provided payment for the health care provider's time and experience in answering the professional survey queries/questions rather than for, for example, answering questions uniquely associated with information provided in the presentation of the information purveyor (i.e., informational queries/questions). Other incentives may include, without limitation, coupons, honorarium, awarding of continuing education credit, free or reduced cost gifts (tangible or intangible), free or reduced-cost access to live, on-line, or hardcopy continuing education courses, physical or electronic "trading stamps," points toward the purchase of an item or service, free or reduced cost consultation time with an expert in an area of interest, and access to information otherwise available on a fee-for-service basis. As would be understood by one of ordinary skill in the art, the incentive provided preferably should take into account opinions by governmental agencies, e.g. FDA and OIG, with respect to which incentives would not violate any "anti-kickback statute or regulation" or the like.

In one embodiment, the incentive provided to the health care provider is a, discount, redeemable points, or other aid (such as food, clothing, heating fuel assistance, objects (such as toys, appliances, pharmaceuticals etc.)) to a charitable organization, such as a non-profit charitable organization, e.g., a 501(c)(3) organization or a religious organization. Thus the time and effort undertaken by the health care provider in providing information to the system may reward the charitable organization in the aid it receives from the health care provider and other similar inclined health care providers (e.g., each provider might donate redeemable points which the charitable organization might use to obtain items of need). For example, a physician, pharmacist, nurse, managed care provider, formulary committee, health care researcher, professional association may be rewarded for responding to certain questions by allowing the same to donate their incentive to the charitable organization.

When information pertaining to a health care providers practice is garnered, survey information from the health care provider may be used, for example, to identify target marketing opportunities, initiate continuing medical education needs assessment for grants, assessment of brand awareness/effectiveness, and/or assess effectiveness of a detailing program. Health care provider attitudes may also be benchmarked, for example, with respect to a particular product, a competitor product, diagnostic procedures, treatment options, opinions of sales representations, and the effectiveness of sample programs. Questions presented to health care providers may be designed to help elicit, for example, thoughts on various dosing regimens, potential new indications, new thoughts pertaining to combination therapies, information pertaining to potential adverse drug interactions and side effects, and management techniques for known side effect. Response from the health care providers can be used to verify or expand data gathered through other methods like IMS. The system may be configured to allow data to be shared among health care provider respondents.

In an optional aspect of such embodiment, the system may be configured (by way, for example by hardware and/or software) to proffer the health care provider using the system a plurality of charitable non-profit organizations to which the health care provider's incentive may be donated. The options may be provided, for example, in a menu format, a display of a number of icons, etc. Alternatively, or in addition, the system may allow the health care provider to input contact information pertaining to a charitable organization that is not proffered by an option selection.

The system may be designed to allow one to retrieve information pertaining to the status and/or goals of the organizations proffered by executing a link to the organization, or to a source of information on the organization.

In yet another embodiment, there is provided a system optionally configured to provide charitable organization options that are based upon input by the health care provider regarding causes of interest to the provider. Thus if a health care provider indicates that the provider is interested, for example, in feeding and/or clothing the poor in Ethiopia, or aiding religious groups persecuted in China, or helping the victims of natural disasters in the United States or abroad, the system may be configured to offer as options for donation, organizations that are specifically dealing with such issues.

In respect to charitable organization options selected by a health care provider, the system may be further configured to selectively provide as a primary option to the health care provider upon reentry of the system one or more charitable organizations previously selected by the health care provider. Thus the history of selections by a particular health care provider may be used to hone the options proffered to the health care provider.

In yet another embodiment, the system provides the health care provider with a number of different incentives that may be provided to the charitable organization. For example, the system may allow a provider to select from different items needed by a charitable organization (for example, an organization sheltering people might need money for the shelter, clothing to keep people warm, food etc.).

In respect to charitable donations, the attribution of the incentive may or may not be attributed to the health care provider. For example, the health care provider may provide the incentive anonymously or in the provider's name. Further, the charitable donation may be tax deductible as provided by the law to the provider of the service, to the health care provider, the charity etc. (for example, marketing, education and research dollars may be tax deductible)

Topic information provided may be in any format, for example static web pages, dynamic web pages, video clips. The topic information provided preferably is related to the profile of the health care provider and the interactive information quizzes, as opposed to professional survey queries/questions, should relate to the information that is ultimately retrieved by the health care provider to be reviewed. Professional survey queries/questions preferably are related to the practical experiences of the health care professional with respect to the health care professional's profession, in particular the health care professional's patient population, and the health care professional's opinions with regard to practice specialty.

Interactive information quizzes and/or professional survey queries/questions may require a response selected from multiple choice options (e.g. multiple choice format) or may require a free-form response (e.g. written). Credit for a response, either in terms of continuing education credit or the incentive credit, may be divisional, for example partial credit being provided for an answer that this not optimum but acceptable, or is correct only in part.

Responses to the professional survey queries and interactive information quizzes are preferably stored, and may be currently, or subsequently, transmitted to a third party with interest in such responses, to one or more participants etc. For example, the responses may be very useful for health care companies, such as pharmaceutical companies, in determining to whom to market their products. For example, an oncologist that has a large number of patients suffering from bone cancer, would be far more likely to be interested in receiving information pertaining to drug used in the treatment of bone cancers than an oncologist whose specializes only in breast cancer. Likewise, a pharmaceutical company could benefit from understanding a physician's method of treating high blood pressure in discerning how best to position their blood pressure medication vis-à-vis such physician's methods. The company could also provide information pertaining to alternate treatment protocols that have been found be effective by other physicians in treating hypertension. The system may also provide e-consult opportunities, a sample & promotional catalogue, links to sites of interest to health care professionals, product libraries of likely interest to the health care provider, continuing medical education opportunities etc.

An embodiment of the system may also be configured to permit the user to provide other feedback information. For example, a health care professional could use the system to contact a sales representative of the health care company, such as drug representative of a pharmaceutical company. Responses from the users could then be used by the representative to improve information flow.

BRIEF DESCRIPTION OF THE FIGURES

A more complete appreciation of the invention and the advantages thereof will be more readily apparent by reference to the detailed description of the preferred embodiments when considered in connection with the accompanying figures, wherein:

FIG. 3 is a screenshot of an exemplary homepage which may be presented to allow select access to information available at the website;

FIG. 5 is a screenshot of an exemplary screen which may be presented to set forth information available for viewing;

DETAILED DESCRIPTION OF THE PREFERRED EMBODIMENTS

Figure 1:
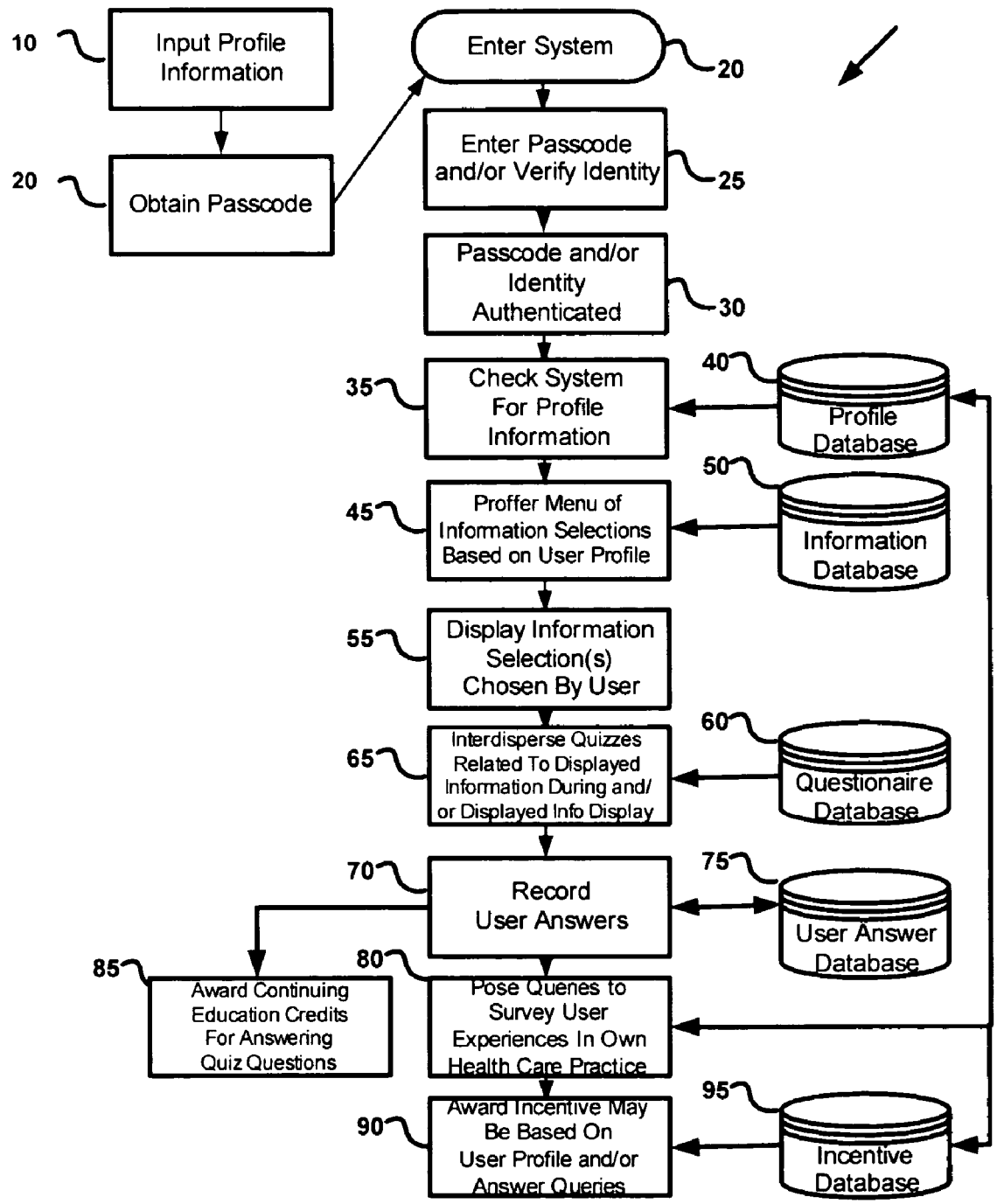
FIG. 1 is a functional schematic overview of an embodiment of the present system and method.

The present invention provides a system and method which offers incentives to health care providers to provide information pertaining to their opinions and health care practice.

The accompanying drawings, which are incorporated in and constitute part of the specification, illustrate embodiments of the invention which may be employed, and together with the general description given above and the detailed description, serve to explain the principles of the invention. Such drawings are only intended to show specific embodiments in which the invention may be practiced, and are not intended to limit the invention as a whole as fully described herein. As would be understood by one of ordinary skill in the art, the present invention need not be practiced with all of the specific details set forth in the drawings and certain alternative equivalents to a described step or product may be employed in lieu of specific elements discussed.

FIG. 1 is a functional schematic overview of an embodiment of the present system and method. System 5 employs a number of concrete steps in the provision of information to a user and obtaining information pertaining the opinions and health care practice of the user. As would be understood by one of ordinary skill in the art, system 5 allows multiple users to receive information and provide feedback to the information. The system may be accessed by a network, internet, etc.

Figure 4:
FIG. 4 is a screenshot of an exemplary screen which may be presented to capture information concerning the profile of a health care provider.

At step 10 user inputs profile information. Input of such profile information may be, for example, by input screen 170 of FIG. 4 which requests personal information pertaining to the user 175. Personal information may include a request to determine the type of incentive the user wishes to obtain for participating in the system 180. Upon receipt of profile information use may receive a pass code as at step 75 or be instructed as how to authenticate identity upon subsequent use of the system. Such pass code or authentication method may be required to be employed, step 25, after entrance into system 5 at step 20. Authentication information is preferably encrypted to prevent unauthorized access to the same from third parties. Authentication may depend on any of numerous mechanisms known in the art. For example, physicians may be confirmed by asking for information that may be confirmed by query of state, federal, professional databases. Limited access to system information or services can be provided even if authentication and verification do not occur. Upon authentication of identity, step 30, system 5 checks at step 35 to determine if user has profile information in profile database 40. If no profile information has been stored in profile database 40 or the information in profile database 40 needs to be updated, the user is prompted for profile information.

Figure 9:
FIG. 9 is a screenshot of an exemplary screen providing a mechanism by which an user obtain information from other than a menu list.

Preferably based on the profile of the user, and the topic information available for review by a user as stored in topic information database 50, the user is proffered a list of topic information selections, for example, 185 of FIG. 5, which would be likely desired by the a user of such profile, step 45. Alternatively, the user can search for topic information related to a topic of interest from a library as at 225 of FIG. 9.

Topic information available to user may be screened initially based on the profession of the user, such as shown in FIG. 3 wherein the information available to physicians 150, registered nurses/physician assistants 155, sales agents 160 and office staff 165 differs. Thus topic information about multiple drugs might be proffered to general practitioners, but not to specialists that employ a lesser number of drugs in their practice. Product information The user then selects the information which the user desires to review, and the information is displayed to the user at step 55. Product information may include interactive detail such as animation and interactivity.

Before, during, and/or after the display of the information quizzes, questions etc. may be posed, step 65, to elicit the degree of understanding of the material and may be used to create positive product usage and better recall. Information quizzes, questions, etc. are preferably chosen from a plurality of possible questions in a questionnaire database 60 based on profile information of the user from profile database 40. Of course, topic questions, if not personalized on the basis of the user's profile, can be included within the information itself. Answers to such information quizzes, questions, etc. preferably are recorded, step 70, and the user associated with the responses in stored user answer database 75. Continuing education credits may be provided for answering such information quizzes, questions etc., step 85, a reduced credits for completion of review of a portion of the material.

Figure 6:
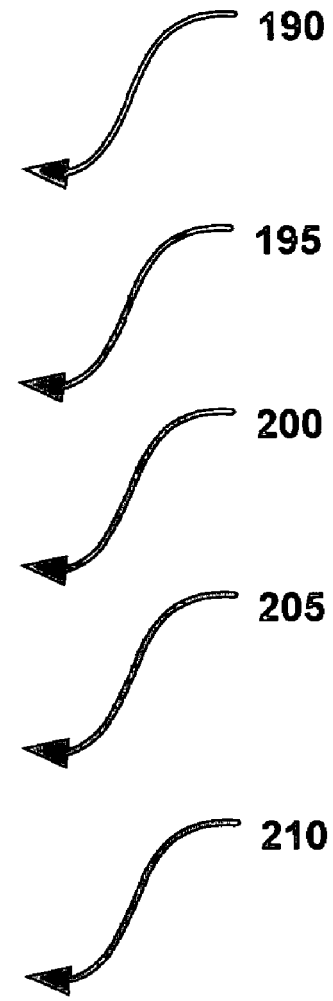
FIG. 6 is a screenshot of an exemplary screen which seeks to obtain survey information concerning a health care provider's practice.

Practice or professional queries are also posed upon review of the information (before, during and/or after presentation of the information), such professional queries surveying user experiences in the user's health care practice and the user's opinions with respect thereto, step 80, for example practice queries as show at FIG. 6 related to increasing incidence of a disease state among a particular age subgroup of the health care provider's patients 190, the percentage of the health care provider's patients within a particular age group 195, the health care provider's approach to treating the patients suffering form the disease state 200, the current medications of a particular therapeutic category the health care provider is using to treat the disease state 205, and the time frame during which the health care provider can most likely be visited personally by a sales representative 210.

Figure 7:
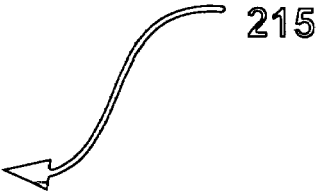
FIG. 7 is a screenshot of an exemplary screen listing account information pertaining to incentives provided to the health care provider for participating in the e-consult.

An incentive is provided based on the response to the professional queries, step 90, preferably such incentive being based on the profile of the user and incentives available, database 95. Incentives may be given to all or a subset of users participating in review of the information and provision of practice information. A running account 215, FIG. 7, may be kept such that the user can determine the incentive levels he has obtained form using the service. Incentives may include credit towards purchase at a vendor's site.

Figure 8:
FIG. 8 is a screenshot of an exemplary screen which sets forth comments by other health care professionals in respect of the information reviewed by the user.

Other services may accompany information delivery and review, as for example, allowing health care providers to communicate among themselves with regard to the joint information they have reviewed through a message board/center 220, FIG. 8. The system may also allow a user to contact the system or third party supplying the information, such as a pharmaceutical company, to report adverse drug reactions, request samples, to request participation in a clinical trial, seek clinical trial data updates, to seek an appointment with a sale representative, to elicit information pertaining to off-label product use, to request patient education material, request reduced-cost medication for indigent patients, etc. The system may also allow the system operators or third parties supplying the information, and their agents, such as detail representatives, to provide urgent information to the user, such as drug recall information by way of system information pertaining to a contact path of the user (email, phone number etc.), marketing information and other information. The system may also provide alternative mechanisms, such as a phone number, mailing address, for the user to contact the information purveyors, or their agents, or system operators and vice versa.

Figure 2:
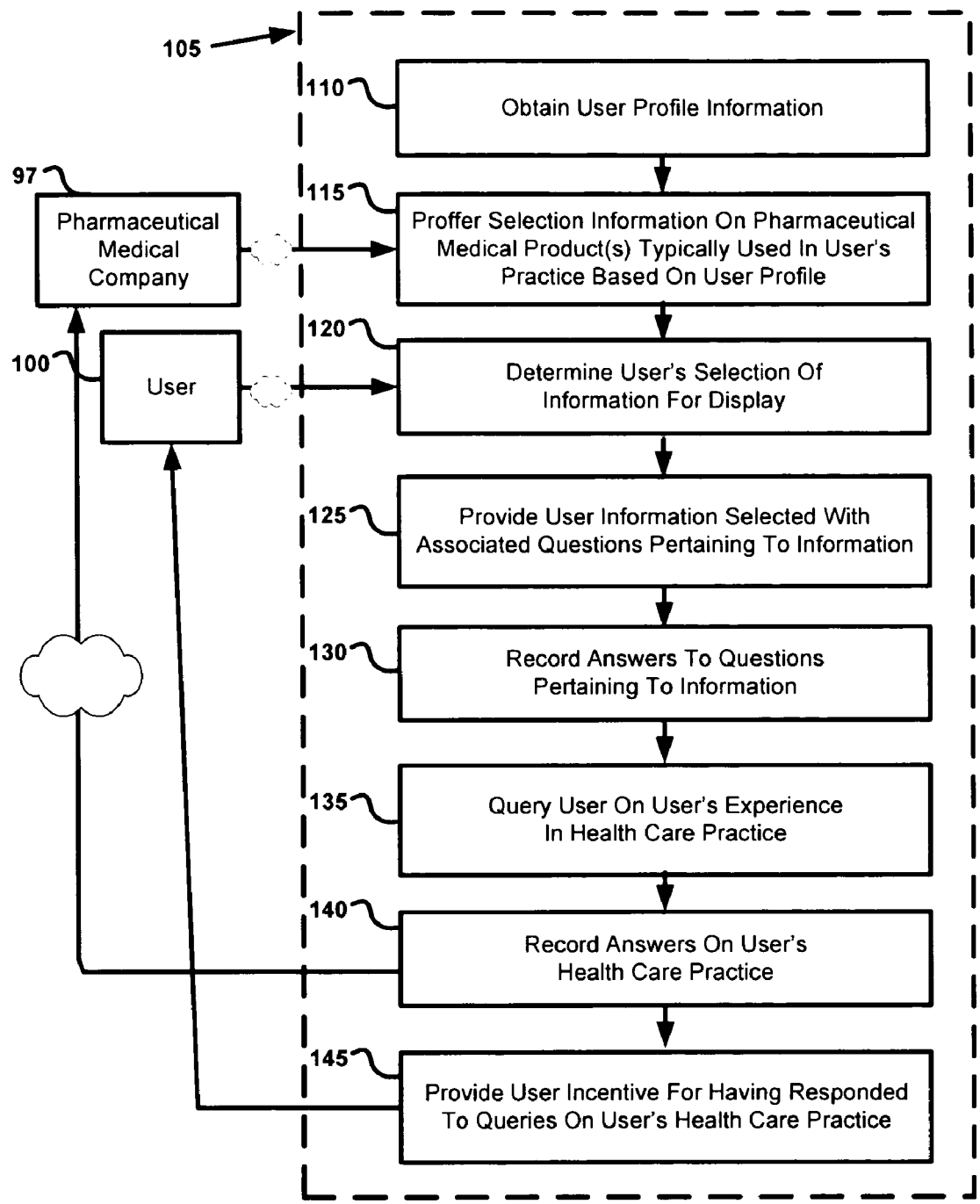
FIG. 2 is a schematic overview of the interplay between parties communicating through an embodiment of the present system and method.

FIG. 2 is a high level schematic overview of the interplay between parties communicating through an embodiment of the present system and method designed to offer health care providers information pertaining to pharmaceutical products and medical supplies. Pharmaceutical and/or medical company 97 proffers a selection of topic information thru system 105 pertaining to pharmaceutical/medical product(s) typically used in a user's practice based on user profile information which is obtained upon entrance into the system, or previously obtained upon entrance into the system, along with questions associated with the content of the topic information, step 115. System 105 upon obtaining profile information pertaining to the user, step 110, proffers topic information selections to the user, and determines the users selection of topic information to be displayed, step 120. The topic information pertaining to such selections is then provided to the user along with the information questions pertaining to the topic information, step 125.

The answers provided by user 100 with respect to the information questions are preferably recorded, step 130, and the user is then queried pertaining to the user's experiences in respect to the health care practice in which the user practices, step 135. Again the answers provided by the user are preferably recorded, step 140, and preferably transmitted to the pharmaceutical and/or medical company for internal marketing and research purposes. The pharmaceutical and/or medical company may alternatively collect information from the system upon request. For providing answers to the practice profile questions or the opinions of the user, the user is provided an incentive at step 145. The incentive may comprise any compensation, including points that may be redeemed at a linked site to purchase physical items such as books, videos, etc. Incentives may be limited to those users whose authorized use is authenticated. The incentive may be supplied to user by any route specified by the user, or known to the system. The system preferably receives the reimbursement for the incentive by the information purveyor, for allowing them access to the information of the users and the ability to directly or indirectly market to the users.

Data pertaining to use of the system, the user's responses, time spent in reviewing information requested, can be stored for further analysis by the system operators or third parties supplying the information, or their agents. Preferably such information is provided or accessible in real-time. Other data, for example URLs accessed by the user may also be stored. Gleaned data may be used to communicate with the user by any mode of communication known (e.g., mail, facsimile, internet). A report can be generated with respect to users, user information, comments, etc. Preferably the data is provided in a manner such that the information purveyor, or its agent can efficiently input such data into their data systems.

Users can be invited to use the system by a host of methods known to those in the art, including by email, postal mail, and advertisement.

In one embodiment of the invention there is provided a system for providing pharmaceutical information to physicians, the system comprising: a physician authentication module configured to authenticate that the user is a registered physician; a presentation hosting module configured to present a plurality of interactive presentations to users that have been authenticated by the physician authentication module, wherein each presentation is related to a prescription drug; and a data accumulation module configured to accumulate user responses to the interactive presentations. Such a system embodiment may further comprise an incentive module configured to provide incentives to users to whom interactive presentations have been presented. Such an incentive module may be further configured to provide incentives only to selected users to whom interactive presentations have been presented, further configured to verify that a user has responded to questions presented in one of the interactive presentations before providing the incentive, and/or further configured to verify that a user has completed participation in one of the interactive presentations before providing the incentive. The data related to users that have viewed presentations may comprise a number of users to which a presentation has been presented, names of users to which a presentation has been presented, and/or responses by the users to the presentations. The system embodiment may further comprise a reporting module configured to provide data related to users that have viewed the presentations and/or a presentation storage module storing the plurality of interactive presentations.

In another embodiment there is provided a method comprising hosting interactive presentations related to prescription pharmaceuticals, accumulating user responses to the interactive presentations, presenting data related to accumulated user responses to drug companies sponsoring the interactive presentations, and providing incentives to users in exchange for participation in the interactive presentations.

In yet another embodiment there is provided a method for providing information related to pharmaceuticals to physicians, the method comprising: (a) inviting a user to access a system configured to provide the information related to pharmaceuticals; (b) through the system, authenticating that the user is a physician; (c) through the system, presenting information related to a pharmaceutical to the user; (d) through the system, prompting the user to provide input confirming the user's comprehension of at least a portion of the presented information; and (e) through the system, receiving input provided by the user in response to (d). Preferably in such method embodiment there is a step of providing an incentive to the user in response to at least (e). The incentive may be a credit that can be redeemed at an on-line vendor and may be provided only to targeted users. Such method embodiment may further comprise the step of: receiving value form a pharmaceutical company in exchange for performing at least (b), (c), (d) and (e). Further, such method embodiment may further comprise the steps of: performing (a), (b), (c), (d), and (e) with respect to a plurality of users; and accumulating input provided by the plurality of users in response to (e). The method embodiment may also comprise a step of: maintaining statistics relating to accumulated input provided by the plurality of users, wherein the statistics may be provided to at least one pharmaceutical company.

As would be understood by one of ordinary skill in the art, steps performed by the system may be embodied in part or whole by human participation. It is preferred that as many steps be automated as possible. Human participation may include analysis and interpretation.

Although the present invention has been described in detail with respect to certain embodiments and examples, as would be understood by one of ordinary skill in the art variations and modifications exist which are within the scope of the present invention as defined in the following claims.

What is claimed is:

1. A computer system for providing incentives to a health care provider to provide information pertaining to the health care provider's practice, said system comprising:

an authentication device operatively configured to authenticate that a health care provider entering the computer system is an authorized user;

a query device operatively configured to proffer at least one practice-related question tailored to the professional profile of said health care provider, said at least one practice-related question pertaining; to experiences and opinions of the health care provider with respect to the health care provider's practice, and being selected from the group consisting of: the health care provider's thoughts on various dosing regimens, potential new indications, combination therapies, potential adverse drug interactions and side effects, and management techniques for known side effects;

the query device being further configured to: dynamically generate surveys based on an answer to said at least one practice-related question, and receive a communication from the health care provider, the communication being selected from the group consisting of: a report of adverse drug reactions, a request for samples, a request for participation in a clinical trial, a request for clinical trial data updates, a request for an appointment with a sale representative, a request for information pertaining to off-label product use, a request for patient education material, and a request for reduced-cost medication for indigent patients;

an incentive device operatively configured to proffer an authenticated provider an opportunity to provide assistance to one or more charitable organization(s) by providing responses to said at least one practice-related question as generated by said query module, wherein the opportunity to provide assistance to the one or more charitable organization(s) is an incentive for the authenticated provider to provide said responses; and an incentive calculation device operatively configured to determine the incentive earned by said health care provider by responses provided to said at least one practice-related question.

2. Computer-readable media comprising instructions that cause a computer to provide aid to charitable organizations, said instructions providing for:

authentication of a user of said computer-readable media as a permitted user of said computer-readable media;

provision of at least one question to said authenticated user, said at least one question: being related to the health care practice of said authenticated user, pertaining to experiences and opinions of said authenticated user with respect to the health care practice of said authenticated user, and being selected from the group consisting of: said authenticated user's thoughts on various dosing regimens, potential new indications, combination therapies, potential adverse drug interactions and side effects, and management techniques for known side effects;

provision of an incentive to said authenticated user for answering said at least one question related to the health care practice of said authenticated user, said incentive comprising a donation to a charitable organization;

transmission of said incentive to said charitable organization upon the authenticated user answering said at least one question;

dynamic generation of surveys based on an answer to said at least one question; and receipt of a communication from said authenticated user, the communication being selected from the group consisting of: a report of adverse drug reactions, a request for samples, a request for participation in a clinical trial, a request for clinical trial data updates, a request for an appointment with a sale representative, a request for information pertaining to off-label product use, a request for patient education material, and a request for reduced-cost medication for indigent patients.

3. The computer-readable media of claim 2, wherein said incentive is selected from the group consisting of: a monetary donation, a tangible or intangible good donation, a point donation redeemable by said charitable organization at defined point level for particular goods, and a discount.

4. The computer-readable media of claim 2 wherein the authenticated user is selected from the group consisting of: a physician, a nurse, a pharmacist, a medical technologist, a physical therapist, and a clinician.

5. The computer-readable media of claim 2, wherein said incentive is transmitted to said charitable organization at a time after said answer to said at least one question is made.

6. The computer-readable media of claim 2, wherein said incentive is transmitted to said charitable organization in real time upon receipt of said answer to said at least one question.

7. A system for providing a health care provider with customized health care information, the system comprising:

a computer that is configured to:

confirm that the health care provider is an authentic health care provider, and submit to the authentic health care provider at least one question, the at least on question: pertaining to experiences and opinions of the health care provider with respect to the health care provider's practice, and being selected from the group consisting of: the health care provider's thoughts on various dosing regimens, potential new indications, combination therapies, potential adverse drug interactions and side effects, and management techniques for known side effects; and an interlace that provides the health care provider with an interactive presentation that includes information relating to a pharmaceutical or medical product or service, the information being selected based on the health care provider's practice, the interface being configured to:

present the health care provider an on-line survey that comprises a quiz that prompts the health care provider's comprehension of at least a portion of the information included in the interactive presentation, and present the health care provider with an incentive for answering the at least one question or quiz, the incentive comprising a donation to a charitable organization, and the computer being further configured to: receive an answer to the at least one question or quiz, cause the charitable organization to receive the donation upon receiving the answer by the health care provider, dynamically generate other surveys based on the answer, and receive a communication from the health care provider, the communication being selected from the group consisting of: a report of adverse drug reactions, a request for samples, a request for participation in a clinical trial, a request for clinical trial data updates, a request for an appointment with a sale representative, a request for information pertaining to off-label product use, a request for patient education material, and a request for reduced-cost medication for indigent patients.

8. The system of claim 7, wherein the donation is selected from the group consisting of: a monetary donation, a tangible or intangible good donation, a point donation redeemable by said charitable organization at a defined point level for particular goods, and a discount.

9. The system of claim 7, wherein the health care provider is selected from the group consisting of: a physician, a nurse, a pharmacist, a medical technologist, a physical therapist, and a clinician.

10. The system of claim 7, wherein the donation is made at a time after the answer to the at least one questions or quiz is received.

11. The system of claim 7, wherein the donation is made in real time upon receipt of the answer to the at least one questions or quiz.

12. The system of claim 7, wherein the on-line survey is presented at a time after the health care provider views the interactive presentation.

13. The system of claim 7, wherein the on-line survey is presented while the health care provider views the interactive presentation.

14. The system of claim 7, wherein the interface is further configured to allow the health care provider to choose the charitable organization to which the donation is made.

15. The system of claim 14, wherein the health care provider is presented with a list of a plurality of charitable organizations to choose from.

16. The system of claim 14, wherein the health care provider is presented with the ability to enter contact information pertaining to the charitable organization of choice.

17. The system of claim 14, wherein the health care provider is presented with one or more causes to choose from.

* * * * *